United States Patent [19]

Balint

[11] Patent Number: 4,863,869
[45] Date of Patent: Sep. 5, 1989

[54] ANTI-HUMAN IGM IMMUNOADSORBENT AND PROCESS FOR PRODUCING SAID IMMUNOADSORBENT

[75] Inventor: Joseph P. Balint, Seattle, Wash.

[73] Assignee: Imre Cororation, Seattle, Wash.

[21] Appl. No.: 194,669

[22] Filed: May 13, 1988

Related U.S. Application Data

[62] Division of Ser. No. 934,235, Nov. 21, 1986, Pat. No. 4,762,787.

[51] Int. Cl.$^4$ .............................................. C12M 1/24
[52] U.S. Cl. .................................. 435/296; 435/176; 436/513; 436/524; 436/823; 530/811
[58] Field of Search ................ 435/176, 288, 296; 436/518, 513, 523, 524, 527, 823; 604/5, 6; 502/402, 403, 412; 530/811; 210/263, 691, 289

[56] References Cited

U.S. PATENT DOCUMENTS

| | | | |
|---|---|---|---|
| 3,652,761 | 3/1972 | Weetall | 424/12 |
| 3,975,511 | 8/1976 | Vann et al. | 424/1.5 |
| 4,059,685 | 11/1977 | Johnson | 424/12 |
| 4,163,779 | 8/1979 | Harte et al. | 424/1 |
| 4,294,817 | 10/1981 | Burgett et al. | 424/8 |
| 4,332,783 | 6/1982 | Pernice et al. | 424/1 |
| 4,434,227 | 2/1984 | Unger | 436/513 |
| 4,436,823 | 3/1984 | Blumcke et al. | 436/169 |
| 4,478,946 | 10/1984 | Van der Merwe | 436/518 |
| 4,614,513 | 9/1986 | Bensinger . | |
| 4,681,870 | 7/1987 | Balint, Jr. et al. | 502/403 |
| 4,705,628 | 11/1987 | Yamamoto et al. | 210/289 |
| 4,716,108 | 12/1987 | Sato et al. | 436/513 |

FOREIGN PATENT DOCUMENTS

| | | |
|---|---|---|
| 0088818 | 9/1983 | European Pat. Off. . |
| 0110409 | 6/1984 | European Pat. Off. . |
| 0131251 | 1/1985 | European Pat. Off. . |
| 0175270 | 3/1986 | European Pat. Off. . |
| 0183207 | 6/1986 | European Pat. Off. . |
| 0237659 | 9/1987 | European Pat. Off. . |
| 59-26066 | 2/1984 | Japan . |
| 59-34828 | 5/1984 | Japan . |
| 59-139036 | 8/1984 | Japan . |
| 59-193135 | 11/1984 | Japan . |

OTHER PUBLICATIONS

Weetall (1971), Research Development, pp. 18–22, "Enzymes Immobilized on Inorganic Carriers".
Weetal, "Immobilized Enzymes . . . Peptides", Publ. Marcel Dekker, I NY, NY (1975), pp. 1–14.
Jones et al. (1980), Cancer, 46:675–684.
Ray et al. (1980), Cancer, 45:2633–2638.
Holohan et al. (1982), Can. Res., 42:3663–3668.
Terman et al. (1981), N. Engl. J. Med., 305:1195–1200.
Balint, Jr. et al. (1984), Cancer Research, 44:734–743.
Weetal (1976), Meth. Enzymol., 44:134–148.
Bensinger et al. (1981), N. Engl. J. Med., 304:160–162.
Bensinger et al. (1982), J. Clin. Apheresis, 1:2–5.
Bensinger et al. (1982), N. Engl. J. Med., 306:935.
"Affinity Chromatography–Affinity Chromatography–Principles and Methods" Published by Pharmacia Fine Chemicals, Uppsala, Sweden.

Primary Examiner—Noah P. Kamen
Attorney, Agent, or Firm—Townsend and Townsend

[57] ABSTRACT

An immunoadsorbent material for removing IgM and IgM-complexes from biological fluids is prepared by covalently binding anti-IgM antibodies to a solid-phase silica matrix. It has been found that reacting hydroxy-derivatized silica in the presence of cyanogen bromide with the anti-IgM antibodies provides a particularly stable, high-capacity immunoadsorbent. The immunoadsorbent material may be employed in a column for therapeutic treatment of various disorders, such as primary biliary cirrhosis.

7 Claims, 2 Drawing Sheets

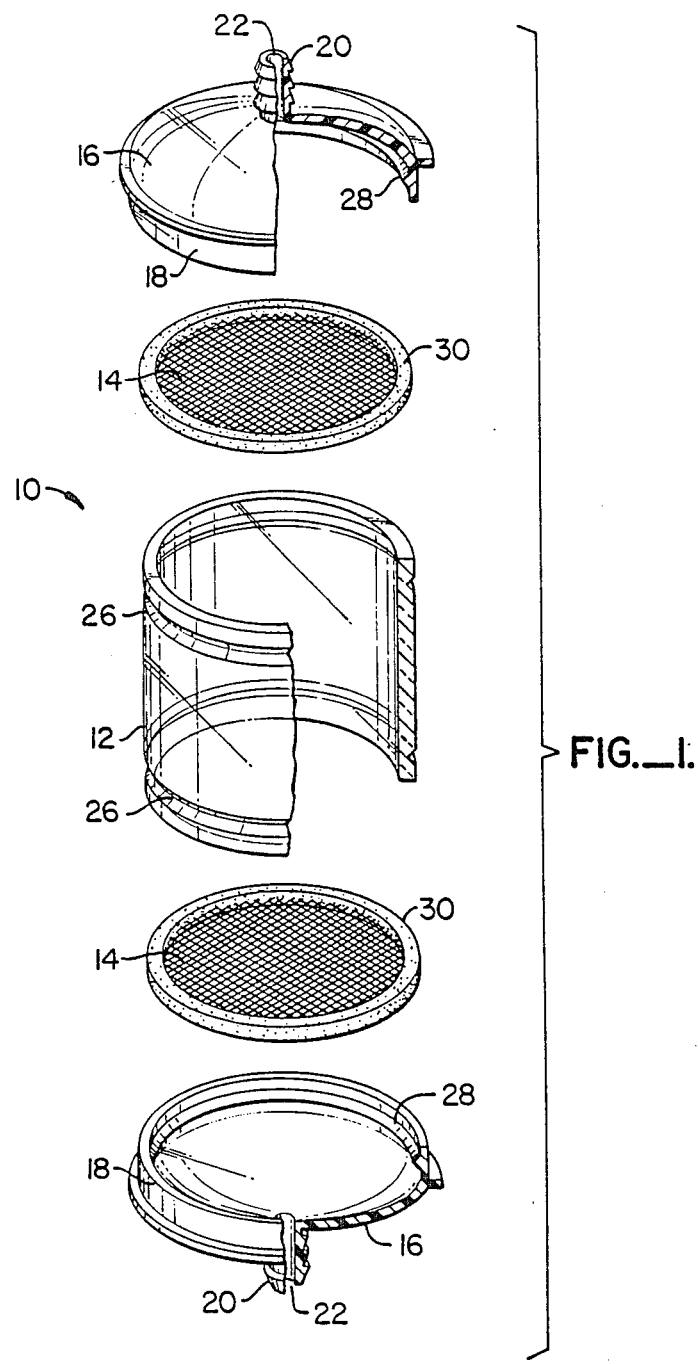
FIG._1.

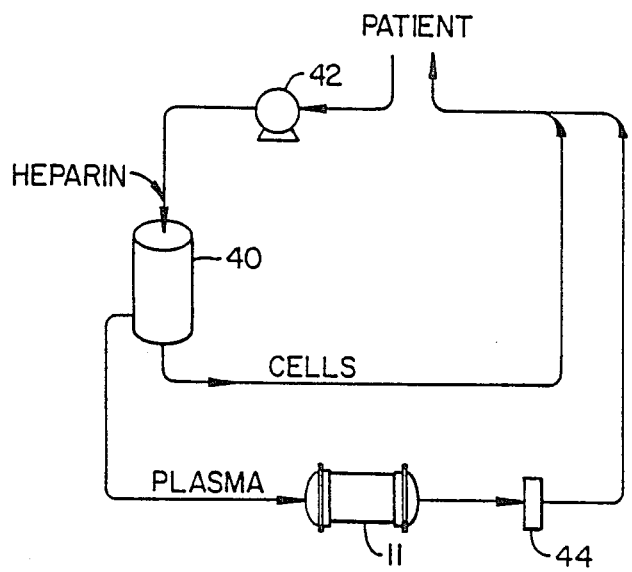
FIG._2.

ANTI-HUMAN IGM IMMUNOADSORBENT AND PROCESS FOR PRODUCING SAID IMMUNOADSORBENT

This is a division of application Ser. No. 934,235, filed Nov. 21, 1986 now U.S. Pat. No. 4,762,787.

BACKGROUND OF THE INVENTION

1. Field of the Invention

The present invention relates generally to materials for the immunologic removal of proteins and other species from biological fluids, and more particularly to an immunoadsorbent material for removing IgM and IgM-related complexes from blood.

The extracorporeal treatment of blood to remove immunoglobulins and circulating immune complexes may be useful in a variety of circumstances. For example, the removal of circulating IgM and IgM-related complexes may have therapeutic value in the treatment of primary biliary cirrhosis (PBC). PBC is a syndrome of disordered immune regulation associated with increased levels of immunoglobulins (primarily IgM) in the blood, increased levels of circulating immune complexes, the presence of auto-antibodies, and altered T and B cell function.

It would be desirable to provide substances capable of removing IgM and IgM-related compexes from a patient's blood. It is particularly desirable that the substances be convenient to use, sterile, and avoid the release of toxic substances into the blood being treated.

b 2. Description of the Background Art

Blood treatment systems for the removal of anti-A and anti-B antibodies are described by Bensinger et al. (1981) N. Engl. J. Med. 304:160-162 and Bensinger et al. (1982) J. Clin. Apheresis 1:2-5. The immunoadsorption system utilizes synthetic human blood group antigens covalently linked to a silica matrix. The use of a protein A-silica column for extracorporeal immunoadsorption is briefly reported by Bensinger et al. (1982) N. Engl. J. Med. 306:935. "Affinity Chromatography - Principles and Methods" published by Pharmacia Fine Chemicals, Uppsala, Sweden, teaches that carbodiimide coupling to Sepharose® is best performed at a pH above 4.5.

SUMMARY OF THE INVENTION

The present invention provides a method for preparing an immunoadsorbent material and a system employing the immunoadsorbent material for the extracorporeal removal of IgM and IgM-related complexes from biological fluids, such as blood and plasma. Such treatment may be useful for the treatment of a variety of disorders, including primary biliary cirrhosis (PBC). The immunoadsorbent material of the present invention is prepared by covalently coupling anti-IgM antibody to a solid-phase silica matrix under particular conditions. The solid-phase silica matrix is either an amorphous or crystalline silica, and covalent coupling is accomplished by introducing free surface groups, such as hydroxyl and amino groups, onto the silica matrix and activating such groups with cyanogen bromide. The activated surface groups react with available groups on the anti-IgM antibodies, resulting in covalent bonding. It has been found that the immunoadsorbents thus prepared have a very high capacity for the adsorption of IgM, are highly stable, and avoid the release of the anti-IgM antibodies and other substances into the biological fluid being treated. In addition, the immunoadsorbent materials are non-toxic and are resistant to the generation of fines during subsequent handling. The adsorbents thus prepared can be air-dried, loaded into biocompatible cartridges, and gas sterilized. The cartridges can then be transported under sterile conditions, rehydrated on site, and employed for clinical treatment in a one-use disposable manner.

BRIEF DESCRIPTION OF THE DRAWINGS

FIG. 1 is an exploded view of the immunoadsorbent column of the present invention.

FIG. 2 is a diagrammatic representation of a system for the extracorporeal treatment of blood constructed according to the present invention.

DESCRIPTION OF THE SPECIFIC EMBODIMENTS

An immunoadsorbent column having a novel immunoadsorbent material therein is provided for the extracorporeal treatment of a biological fluid, such as blood or plasma, to remove IgM and IgM-complexes therefrom. The novel immunoadsorbent material of the present invention comprises anti-IgM antibodies covalently coupled to a solid-phase silica matrix under particular conditions which have been found to maximize the activity and reactivity of the antibody while minimizing leakage of the antibody and other substances from the column during use. The treatment may be provided by continuously removing a patient's blood, separating the blood cells therefrom, treating the separated plasma in the immunoadsorbent column to remove the IgM and IgM-complexes, and mixing and returning the treated plasma and blood cells directly to the patient. Alternatively, where only partial removal of IgM and IgM complexes is desired, the blood cells may be directly reinfused into the patient after a limited quantity of blood has been removed and the blood cells separated. The separated plasma may be collected, treated in the immunoadsorbent column of the present invention, and then returned to the patient as early as possible.

Antibodies to IgM are commercially available, or may be obtained as follows. Normal human IgM may be obtained from pooled sera, and antibodies obtained by injecting the purified IgM into a wide variety of vertebrates in accordance with conventional techniques. The injections will usually be repeated on a predetermined schedule, and the vertebrates bled periodically with successive bleeds having improved titer and specificity. The IgM antigen may be injected intramuscularly, intraperitoneally, subcutaneously, or the like. Usually a vehicle is employed, such as complete or incomplete Freund's adjuvant. If desired, monoclonal antibodies may be prepared according to the now classic teachings of Kohler and Milstein (1976) Eur. J. Immunol. 6:511–519.

The solid-phase silica matrix may comprise virtually any form of particulate silica, including amorphous silicas, such as coloidal silica; silica gels; precipitated silicas; fumed silicas; microcrystalline silicas, such as diatomites; and crystalline silicas, such as quartz. The silica should have a particle size in the range from about 45 to 120 mesh, usually in the range from 45 to 60 mesh.

In the preferred embodiment, the solid-phase matrix of the immunoadsorbent material will be formed from diatomite aggregates. Usually, the diatomite material will be calcined to remove any remaining organic material and to harden the surface of the aggregates in order to lessen breakage and degradation of the immunoadsorbent during use. The diatomite material consists primarily of silica (silicon dioxide) with lesser amounts of other minerals, including aluminum oxide, calcium oxide, magnesium oxide, ferric oxide, and the like. Usually, the diatomite material will comprise at least 80% silica, with less than 5% by weight of any other single mineral. Other impurities may be present in the diatomite, but care should be taken that such impurities are non-toxic and non-degradative to the biological fluid being treated. A particularly suitable solid-phase silica (diatomite) matrix may be obtained from Johns-Mannville Corporation under the trade name Chromosorb ®.

The anti-IgM antibodies are covalently coupled to the solid phase silica matrix by a derivatizing matrix to introduce reactive hydroxyl groups, and reacting the derivatized matrix with cyanogen bromide (CNBr). It has been found by the inventor herein that other methods for binding the anti-IgM antibodies to the silica matrix are ineffective, providing little or no binding of functionally active anti-IgM antibody to the silica matrix. The details of the various binding protocols, and the results of such protocols, are set forth in detail in the Experimental section hereinafter.

Generally, the coupling protocol of the present invention is as follows. Free surface groups, including amino groups and hydroxyl groups (in addition to those hydroxyl groups occuring in the native structure of the matrix) may be introduced to the silica matrix by any suitable method. For example, to add hydroxyl groups, the silica matrix may be acid washed, rinsed extensively with water, and dried. The acid washed silica is then reacted in a 5 to 10% solution of a silane, such as $\gamma$-aminopropyltriethoxysilane or $\gamma$-glycidoxypropyltrimethoxysilane. After a short incubation, typically about 1 to 5 hours at 75° C., the silica matrix is again washed extensively with water and dried at an elevated temperature, typically 100° C.

The cyanogen bromide coupling is then carried out as follows. Cyanogen bromide is dissolved in water, and the silica matrix is added to the water with the pH adjusted to about 11 to 11.5. The cyanogen bromide solution is added to the silica matrix, and the mixture is constantly stirred keeping the silica particles in suspension. The pH is maintained in the range between 11.0 and 11.5 by adding NaOH until pH stabilization occurs. The activated silica matrix is extensively washed with water, mixed with a solution of the anti-IgM antibody, the pH adjusted to the range from 8.5 to 9.0, and the mixture held at 25° C. for several hours, typically from 2 to 18 hours. After coupling, the matrix is washed extensively with water, dried, and washed one time in an acid wash, pH 3.5, to remove non-covalently bound and acid labile antibody linkages. The silica matrix is then washed in water for a final time and checked for pyrogens.

Referring now to FIG. 1, the construction of a suitable cartridge 10 for containing the immunoadsorbent material as just described is illustrated. The cartridge comprises a cylinder 12, a pair of retaining screens 14, and a pair of end caps 16. The end caps 16 each include a flange element 18 projecting from one surface thereof and a connector nipple 20 projecting from the other surface thereof. The connector nipple includes an axial passage 22 therethrough to define inlet/outlet ports 24 through the end caps 16. The cylinder 12 includes an annular groove 26 at each end thereof. The flange element 18 on each end cap 16 includes a mating ring 28 on the inner cylindrical surface thereof, which mating ring engages the annular groove 26 when the caps are placed over the end of the cylinder 12. Each screen 14 includes a gasket 30 around its circumference, which gasket serves as a sealing member between the end caps 16 and the cylinder 12 when the cartridge 10 is assembled. To assemble cartridge 10, a first screen 14 is placed over one end of the cylinder 12, and an end cap 16 is fitted over the screen 14. The cylinder 12 is then filled with the immunoadsorbent material as described above, and the assembly of the cartridge is completed by placing the remaining screen 14 and end cap 16 in place. The dimensions of the cartridge 10 are not critical, and will depend on the desired volume of the immunoadsorbent material. The volume of cylinder 12 will typically range from about 50 to 500 cc, having a diameter in the range from about 4 to 8 cm and a length in the range from about 5 to 10 cm. A column 11 (FIG. 2) which comprises a cartridge 10 containing a suitable amount of the immunoadsorbent material prepared as described above, may be sterilized, typically with a gas sterilant such as ethyleneoxide, and either used immediately or sealed and stored for later use. Prior to use, the column 11 will be washed with normal saline followed by a wash with normal saline containing heparin or other suitable anti-coagulant such as anti-coagulant citrate dextrose (ACD). The column 11 may then be connected to a cell separator 40 (FIG. 2) to receive separated plasma therefrom. The cell separator 40 may be a continuous flow cell separator, such as an IBM Model 1997, available from IBM, Armonk, N.Y., or may comprise a semi-permeable membrane which allows passage of the plasma and blood proteins, but prevents passage of the cellular elements of the blood. In the case of a semi-permeable membrane, a blood pump 52 will be required to pass the blood through the membrane. Suitable blood pumps include tube and peristaltic pumps where the blood is isolated from the pumping machinery to prevent contamination. The blood will pass through the cell separator 40 at a rate in the range from about 10 to 20 ml/min. typically until a total volume of about 2 liters of blood have been passed. The blood cells are then mixed with the plasma passing from the treatment column 11, and the recombined blood returned to the patient. Typically, a microfilter 44 is provided at the outlet of the treatment column to prevent passage of macroscopic particles which might be lost from the column 11.

The following examples are offered by way of illustration, not by way of limitation.

EXPERIMENTAL

1. Antibodies to human IgM

Normal human IgM was isolated from sera, as described by Balint et al. (1981) Immunol. Communications 10:533. Five ml of sera were subjected to G-200 column chromatography (3.5×95 cm column in phosphate buffered saline (PBS), pH 7.5), and the excluded volume fractions were incubated with immobilized protein A. The protein A column was extensively washed with phosphate buffered saline (PBS), and bound IgM was eluted with acid PBS, pH 2.5. The eluted IgM was neutralized, concentrated, and the purity was confirmed in double immunodiffusion gel studies and polyacrylamide gel electrophoresis (PAGE) studies.

Antisera to the purified human IgM was prepared by immunizing three rabbits, as described by Balint (1982) Clin. Exp. Immunol. 47:70. To remove human light chain reactivity, the rabbit antiserum was adsorbed with purified human IgG coupled to Sepharose® 4B. Rabbit antibody to human $\mu$ chain of IgM was then affinity purified by adsorption with purified human IgM coupled to Sepharose® 4B. Bound affinity purified rabbit immunoglobulin was eluted with acid PBS, pH 2.5, neutralized, and concentrated. The affinity purified rabbit antibody showed a single precipitin band with normal human serum and formed a line of identity with purified human IgM. There was no reaction with human IgG. Polyacrylamide gel electrophoresis analysis of the affinity purified rabbit antisera revealed polypeptide chains corresponding to $\gamma$ and light immunoglobulin chains of rabbit IgG.

Affinity purified goat Ig-antibody to human $\mu$ chain of IgM was purchased from Cappel Laboratories. Analysis of the Cappel antibody showed a single precipitin band with normal human serum and formed a line of identity with purified human IgM; there was no reaction with human IgG. Purified goat IgG antibody to human $\mu$ chain of IgM was also purchased from Sigma Chemical. The Sigma antibody to human $\mu$ chain was further affinity purified by adsorption with purified human IgM coupled to Sepharose® 4B. In double immunodiffusion studies, the Sigma IgG showed a single precipitin band with normal human sera and formed a line of identity with purified human IgM. There was no reaction with purified human IgG.

2. Activated Silica

The silica matrix employed in the following experiments was acid-washed Chromasorb®P, No. C5889, Johns-Manville.

3. Covalent Coupling Protocols a. Glutaraldehyde coupling.

Silica matrix was placed in a 10% solution of $\gamma$-aminopropyltriethoxysilane in water, and the pH was adjusted to 3.0. The mixture was heated at 80° C. for 2 hours, washed with water and dried overnight at 115° C. The silica matrix was activated by incubating in a 2.5% solution of glutaraldehyde at pH 7.0 for 1 hour at 25° C. After incubation, the matrix was washed thoroughly with water and incubated with antibody at pH 7.0 for 2 hours at 25° C. The quantity of antibody bound was determined, and the matrix washed thoroughly with water.

b. Coupling with carbodiimide.

The silica matrix was prepared in a. above. To 1 gram of the silica matrix was added 5 mg of antibody and 50 mg of 1-cyclohexyl-3(2-morpholinoethyl)carbodiimide metho-p-toluenesulfonate. The pH was adjusted to 3.5 and the mixture agitated at 25° C. for 18-22 hours. After incubation, the quantity of bound antibody was determined and the matrix washed thoroughly with water.

c. Coupling with cyanogen bromide

The silica matrix was prepared as in a. above. The silica matrix was activated by mixing 5-10 grams of cyanogen bromide per gram silica and maintaining the pH at 11 to 11.5 until a steady baseline reading at this pH was achieved. After washing the matrix thoroughly with water, 5 mg of antibody per gram of silica was added, the pH adjusted to 8.6, and the mixture agitated at 25° C. for 2-18 hours. After incubating, the quantity of bound antibody was determined, and the matrix washed thoroughly with water.

4. Results of Covalent Linkage Studies

Initially, coupling techniques were compared by coupling affinity purified rabbit anti-light chain antibody produced as a by-product in the production of anti-$\mu$ chain rabbit IgG. With both techniques, antibody (1.725 mg) was coupled to silica and assessed for the binding of purified human IgG. Small columns (1 g) of the anti-light chain antibody coupled to silica were constructed and incubated with human IgG. A control column of silica (1 g) without coupled antibody was also incubated with human IgG. The columns were washed, and bound IgG eluted with glycine-HCl, pH 2.5. The quantity of eluted IgG was measured by the method Lowry et al. (J. Biol. Chem. (1951) 193:265), and representative results are presented in Table 1.

TABLE 1

| Covalent Coupling Method | IgG Bound |
|---|---|
| Glutaraldehyde Coupling | 1.68 mg |
| Carbodiimide Coupling | 0.66 mg |
| Control Silica | 1.80 mg |

As can be seen from the results in Table 1, there was apparently no specific binding of the human IgG onto the columns. The functionality of the anti-light chain antibody, however, was confirmed in double immunodiffusion studies by the formation of precipitin bands with normal human sera and purified human IgG. Thus, the results suggested that neither the glutaraldehyde or carbodiimide coupling techniques are suitable for the binding of functionally active antibody to the silica matrix.

To confirm the above results, additional experiments were performed employing purified staphylococcal protein A (SpA) obtained from IMRE Corporation, Seattle, Wash. The SpA was coupled to silica by both the glutaraldehyde and carbodiimide techniques. SpA binds to mammalian IgG via the Fc region and, therefore, provides a useful regent to assess the functionality of a product coupled to silica. Small columns (1g) of SpA coupled to silica were constructed and incubated with human IgG. The columns were then washed extensively with PBS, and bound IgG eluted with acid glycine-HCl, pH 2.5. The quantity of eluted IgG was measured by the method of Lowry et al., supra., and representative results are presented in Table 2.

TABLE 2

| Covalent Coupling Method | IgG Bound |
|---|---|
| Glutaraldehyde Coupling (1.79 mg SpA) | 5.40 mg |
| Carbodiimide Coupling (1.96 mg SpA) | 2.28 mg |
| Control Silica | 1.80 mg |

As shown in Table 2, glutaraldehyde coupling results in a functionally active immunoadsorbent material. Based on this result glutaraldehyde coupling was further assessed for suitability in preparing the anti-IgM immunoadsorbent of the present invention.

In a series of experiments, IgG was coupled to silica by the glutaraldehyde method, and it was observed that the coupling efficiency was variable, ranging from 10% to 92.5%. The variability was not apparently associated with the ratio of protein to the silica in the coupling reaction. (ratios of 10:1, 8:1, 6.4:1, 4.8:1, 4:1 and 3.5:1) Moreover, the result is in contrast to coupling of SpA to silica where greater than 95% coupling efficiency can be consistently achieved.

Affinity purified rabbit anti-human μ chain IgG was then coupled to silica in two independent trials employing the glutaraldehyde method. Coupling efficiencies were 46.6% and 57.9% respectively. Small one gram columns of rabbit anti-human μ chain IgG/silica were constructed containing 1.95 mgs and 2.75 mgs of antibody, respectively. One ml of normal human plasma was incubated in each column and in a control column containing one gram of activated silica alone. The columns were washed, extensively with PBS, eluted with acid PBS, pH 2.5, neutralized, concentrated, and the concentration of protein measured as described above. Polyacrylamide gel electrophoresis analysis of the eluates revealed similar polypeptide profiles in all samples. The predominant polypeptides were those corresponding to serum albumin and the γ and light chains of IgG. The presence of two predominant proteins corresponding to human albumin and IgG were confirmed in double immunodiffusion gel studies. IgM was not detected in double immunodiffusion studies.

In comparative control studies, rabbit anti-μ chain IgG was coupled to cyanogen bromide activated Sepharose® 6MB. One ml of normal human plasma was incubated in a small column and in a control column containing uncoupled agarose. The columns were washed extensively with PBS, eluted with acid PBS, pH 2.5, neutralized, and concentrated. The presence of IgM in the eluate from the antibody column, but not the control column, was confirmed in double immunodiffusion studies. It therefore appeared that the glutaraldehyde coupling method did not result in the binding of functionally active anti-IgM antibody to silica for removal of IgM.

To assess the suitability of the cyanogen bromide method for coupling anti-IgM antibody to a silica matrix, affinity purified goat IgG antibody to human μ chain was coupled to silica in five independent trials. Coupling efficiencies ranged from 60% to 97%, resulting in up-takes of 2.79 to 5.33 mg IgG antibody per gram of silica. Small 2 gram columns of the goat IgG antibody coupled to silica were constructed, washed with PBS, and incubated with normal human sera (0.7 cc). After incubation (five minutes at 25° C.), the sera was collected and concentrated to their initial starting volumes and protein concentrations employing negative pressure dialysis as described by Balint (1982), supra. Seven serum samples were incubated in this manner with the immunoadsorbent matrix to determine the maximum binding capacity of the immunoadsorbent. The columns were washed extensively with PBS, pH 7.5, bound protein(s) eluted with acid PBS, pH 2.5, neutralized, and concentrated. The quantity of IgM in pre- and post-immunoadsorption sera were determined by the method of Mancini et al. (1965) Immunochemistry 2:235, and the results are shown in Table 3:

TABLE 3

| Sample | mg IgM/dl Pre-adsorption | Post-adsorption | Percent Reduction |
|---|---|---|---|
| A | 112 | 48 | 57 |
| B | 205 | 150 | 27 |
| C | 150 | 78 | 48 |
| D | 280 | 112 | 60 |

TABLE 3-continued

| Sample | mg IgM/dl Pre-adsorption | Post-adsorption | Percent Reduction |
|---|---|---|---|
| E | 280 | 0 | 100 |
| F | 350 | 112 | 68 |
| G | 67 | 31 | 54 |

As shown in Table 3, significant reductions in levels of IgM were achieved. Further studies were performed to immunochemically assess the presence of human IgM in the column eluates. PAGE studies revealed the presence of polypeptide chains corresponding to μ and light immunoglobulin chains of human IgM in elutes from the immunoadsorbent columns. Double immunodiffusion analyses confirmed the presence of IgM in eluted protein(s) from the immunoadsorbent, but not control columns. These results demonstrated that an anti-IgM immunoadsorbent matrix could be developed and employed in immunoadsorbent affinity chromatography.

Studies were performed to investigate the levels of IgM in serum from patients with primary biliary cirrhosis (PBC). The quantity of IgM in normal and PBC sera were determined by the radial immunodiffusion method of Mancini et al., supra. Substantially higher levels of IgM were detected in PBC serum samples an immunopathologic feature of PBC.

Further studies were performed to determine if the anti-human μ chain/silica columns could reduce the levels of IgM in pathologic sera from patients with PBC. Small columns of anti-human μ chain/silica were constructed, washed with PBS, and incubated with normal or PBC sera. After incubation, the sera were collected and concentrated to their initial starting volumes and protein concentrations employing negative pressure dialysis as described above. The quantity of IgM in pre- and post-immunoadsorption sera were determined by the method of Mancini et al., supra., and the results are shown in Table 4:

TABLE 4

| Sample | mg IgM/dl Pre-adsorption | Post-adsorption | Percent Reduction |
|---|---|---|---|
| A | 4500 | 580 | 87 |
| B | 600 | 0 | 100 |
| C | 1850 | 215 | 88 |
| D | 450 | 112 | 75 |
| E | 385 | 128 | 67 |
| F | 1050 | 280 | 73 |
| G | 850 | 360 | 58 |

As shown in the above table, significant reductions in levels of IgM in the PBC sera were achieved.

An additional experiment was performed to assess the specificity of the immunoadsorbent matrix. To assess specificity, PBC serum samples were incubated with silica matrices coupled to either the anti-μ chain antibody or SpA. After incubation, the sera were collected and concentrated to their initial starting volumes. The quantity of IgM in pre- and post-immunoadsorbed serum was determined by the method of Mancini et al., supra., and substantial reductions in levels of IgM were observed after incubation with the anti-IgM immunoadsorbent but not with the SpA/silica matrix.

Further studies were also performed, employing the anti-μ chain immunoadsorbent as described above, to determine the level of immune complexes (IC) in pre- and post-immunoadsorption sera as assessed in a solid phase C1q binding IgG assay, as described by Balint et al. (1984) Cancer Res. 44:734. The results are shown in Table 5:

TABLE 5

| Sample | μ Equivalents IC/ml | Percent Reduction |
| --- | --- | --- |
| Normal Human Sera Pool | 22.2 ± 5.0 | — |
| PBC sample A Pre-adsorption | 37.0 ± 2.6 | — |
| PBC sample A Post-adsorption | 22.2 ± 2.5 ($p < .01$) | 40% |
| PBC sample B Pre-adsorption | 21.2 ± 1.8 | — |
| PBC sample B Post-adsorption | 16.9 ± 1.2 ($p < .01$) | 20% |

As shown in Table 5, significant reductions in levels of IC in PBC sera were also achieved indicating that the immunoadsorbent column removed immune complexes.

5. Stability of the Matrix

To assess the stability of the anti-μ chain IgG coupled to the silica matrix, and experiment was performed employing a modification of a previously described technique of McConahey and Dixon (1966) Int. Arch. Allergy Appl. Immunol. 29:185. Purified rabbit IgG was radiolabelled with $^{125}I$ to a mean specific activity of 928 cpm per nanogram IgG. Ten μg of the $^{125}I$ IgG was mixed with 6.5 mg of unlabelled rabbit IgG and coupled to 2 grams silica employing the cyanogen bromide method. Uptake of radiolabel and total protein were 96.1% and 99.5%, respectively. After coupling, the IgG/silica was extensively washed and dried. A small column was constructed containing 1 gram IgG/silica (containing approximately $4.64 \times 10^6$ cpm), re-hydrated, and washed with 40 ml PBS. One ml of normal human plasma was added to the column and incubated with the matrix for 5 minutes at 25° C., and fractions were collected until counts approached steady baseline levels (12 fractions). The total counts were accumulated and, based upon the specific activity of the $^{125}I$ IgG, it was estimated that 4–5 nanograms of IgG were released into plasma. This represents about 0.09% of the labelled IgG coupled to the silica. These results demonstrate that an immunoadsorbent matrix with a high degree of stability is constructed by the coupling method of the present invention.

Although the foregoing invention has been described in some detail by way of illustration and example for purposes of clarity of understanding, it will be obvious that certain changes and modifications may be practiced within the scope of the appended claims.

What is claimed is:

1. A system for removing IgM and IgM-related complexes from biological fluids, said system comprising:
    an enclosure having an inlet and an outlet defining a chamber therebetween; and
    immunoadsorbent material packed inside said chamber, said immunoadsorbent material comprising anti-IgM antibody bound to a silica matrix through hydroxyl groups activated with cyanogen bromide.

2. An immunoabsorbent material useful for removing IgM and IgM-related complexes produced by the following method:
    introducing free hydroxyl groups onto a silica matrix;
    activating the hydroxyl groups on silica matrix in the presence of cyanogen bromide at a pH in the range from 11.0 to 11.5; and
    reacting the activated silica matrix with anti-IgM antibody to covalently link the antibody to the activated silica substrate.

3. An immunoadsorbent material useful for removing IgM and IgM-complexes from biological fluids, said immunoadsorbent comprising anti-IgM antibody covalently bound to a silica matrix through hydroxyl groups activated with cyanogen bromide.

4. An immunoadsorbent material as in claim 3, wherein the hydroxyl groups are introduced to the silica matrix by reaction with γ-aminopropyltriethoxysilane.

5. An immunoadsorbent material as in claim 3, wherein the silica matrix is amorphous silica.

6. An immunoadsorbent material as in claim 5, wherein the amorphous silica is diatomite.

7. An immunoadsorbent material as in claim 6, wherein the diatomite is 45 to 60 mesh.

* * * * *